United States Patent [19]

Nakamoto et al.

[11] Patent Number: 4,788,330

[45] Date of Patent: Nov. 29, 1988

[54] POLYPRENYL COMPOUNDS

[75] Inventors: Kouji Nakamoto, Tsuchiura; Takeshi Suzuki; Shinya Abe, both of Ushikumachi; Kenji Hayashi; Akiharu Kajiwara, both of Yatabemachi; Isao Yamatsu, Ushikumachi; Issei Otsuka, Niihari; Hiroyuki Shiojiri, Yatabemachi, all of Japan

[73] Assignee: Eisai Co., Ltd., Tokyo, Japan

[21] Appl. No.: 37,472

[22] Filed: Mar. 7, 1986

[30] Foreign Application Priority Data

Mar. 15, 1985 [JP] Japan .................................. 60-50544

[51] Int. Cl.[4] ............................................. C07C 63/04
[52] U.S. Cl. .................................... 562/493; 562/495; 562/496; 564/182
[58] Field of Search ..................... 562/493, 495, 496; 564/182; 514/570, 571, 568; 511/617

[56] References Cited

PUBLICATIONS

Dawson, J. Med. Chem. 1981 24, 583–592.

Primary Examiner—Paul J. Killos
Attorney, Agent, or Firm—Flynn, Thiel, Boutell & Tanis

[57] ABSTRACT

A polyprenyl compound terminated with a group of

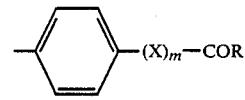

is novel and useful as an antihypercholesterolemic agent and an antiarteriosclerotic agent, in which X is a group of the formula

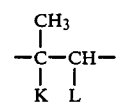

(wherein K and L are independently a hydrogen atom or form a single valence bond between the carbon atoms to which they are attached), a group represented by the formula $-CH_2-$ or a group represented by the formula $-(CH_2)_2-$, m is an integer of 0 or 1, and R stands for a hydroxy group, a group represented by the formula

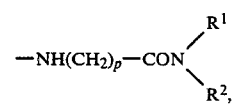

wherein $R^1$ and $R^2$ may be the same or different and each stands for a hydrogen atom or a lower alkyl group and p stands for an integer of 1 or 2, a group represented by the formula $-NH-(CH_2)_q-OH$ (wherein q denotes an integer of 1 or 2) or a group represented by the formula

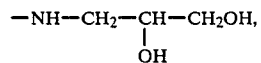

11 Claims, No Drawings

POLYPRENYL COMPOUNDS

The present invention relates to a polyprenyl compound having an excellent pharmaceutical activity.

Particularly, the present invention relates to a polyprenyl compound represented by the general formula (I)

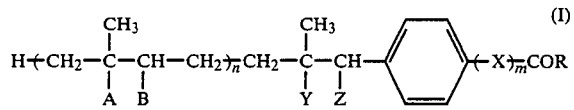

wherein all of A, B, Y and Z stand for hydrogen atoms, or A and B, and Y and Z, each form a single valence bond between the carbon atoms to which they are attached, n stands for an integer of 0 to 2, X stands for a group represented by the formula

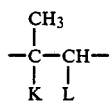

(wherein K and L are independently a hydrogen atom or form a single bond between the carbon atoms to which they are attached, a group represented by the formula —CH$_2$— or a group represented by the formula —(CH$_2$)$_2$—, m is an integer of 0 or 1, and R stands for a hydroxyl group, a group represented by the formula

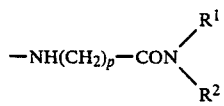

(wherein R$^1$ and R$^2$ may be the same or different and each stands for a hydrogen atom or a lower alkyl group and p stands for an integer of 1 or 2), a group represented by the formula —NH—(CH$_2$)$_q$—OH (wherein q denotes an integer of 1 or 2) or a group represented by the formula

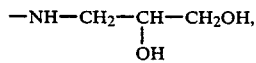

a pharmacologically acceptable salt thereof, a process for the preparation thereof and a pharmaceutical composition containing it.

The lower alkyl defined as R$^1$ and R$^2$ in the general formula (I) is a straight or branched alkyl group having 1 to 6 carbon atoms such as methyl, ethyl, n-propyl, n-butyl, isobutyl, 1-methylpropyl, tert-butyl, n-pentyl, 1-ethylpropyl, isoamyl or n-hexyl.

Though the compound of the present invention can be present as various stereoisomers, the present invention includes all of the stereoisomers.

Examples of the pharmacologically acceptable salts according to the present invention include salts of benzoic acid derivatives represented by the general formula (I) wherein R is a hydroxyl group with metals (for example, sodium, potassium or aluminum) and bases (for example, ammonium, triethylamine, hydrazine, guanidine, dicyclohexylamine, quinine or cinchonine).

All of the polyprenyl compounds according to the present invention are novel compounds which have not been described in literature as yet, and have an excellent cholesterol-decreasing activity, so that they are useful as an antihypercholesterolemic agent and can be used to treat arteriosclerosis.

Up to this time, no polyprenyl compounds having an antihypercholesterolemic and antiarteriosclerotic activity have been known. The inventors of the present invention have long studied various polyprenyl compounds and have found unexpectedly that the polyprenyl compounds according to the present invention have an excellent antihypercholesterolemic activity. The present invention has been accomplished on the basis of this finding.

The compounds (I) according to the present invention can be prepared by various methods. Representative ordinary methods are follows:

Preparation Process 1

The compound represented by the general formula (I) wherein m is 0 and R is OH, i.e.,

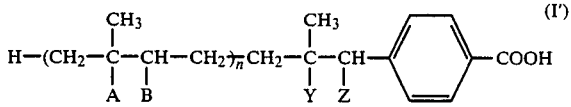

can be prepared by the following procedure.

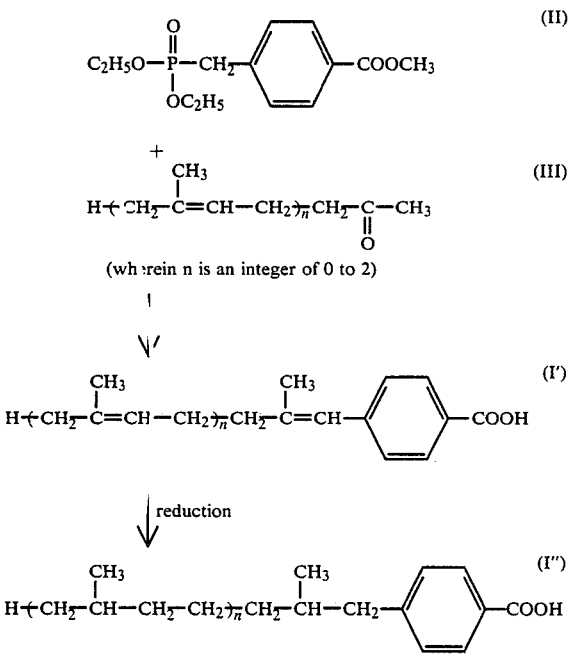

Diethyl (4-methoxycarbonylphenyl)methylphosphonate represented by the formula (II) is reacted with a ketone compound represented by the formula (III) (Wittig reaction), followed by hydrolysis to obtain a compound (I') which is one of the objective compounds. The compound (I') is catalytically reduced to obtain a compound (I") which is also one of the objective compounds. Examples of the catalyst to be used in the Wittig reaction include sodium methylate (MeONa), sodium ethylate (EtONa), t-BuOK and NaH, while examples of the solvent to be used in the Wittig reaction include tetrahydrofuran (THF), dimethylformamide (DMF), ether, nitromethane and dimethyl sulfoxide (DMSO). The reaction temperature is preferably from room temperature to about 100° C.

Preparation Process 2

The compound represented by the general formula (I) wherein m is 0 and R is OH, i.e.,

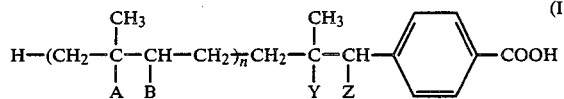 (I')

can be prepared by the following procedure.

[Step I]

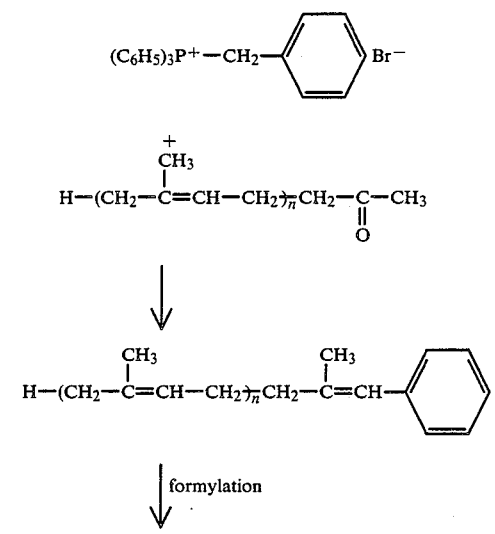

[Step II]

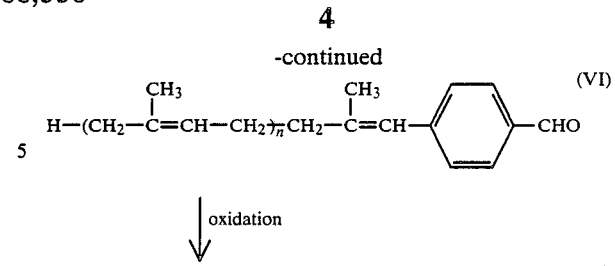 (VI)

↓ oxidation

[Step III]

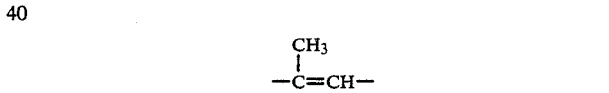 (I')

The reaction of Step I is carried out in the presence of a base such as sodium methylate, sodium ethylate, t-BuOK, MeLi, n-BuLi or $C_6H_5Li$ in a solvent such as ethanol, methanol, tetrahydrofuran (THF), ether, dimethylformamide (DMF) or dimethyl sulfoxide (DMSO), preferably at a temperature of from room temperature to about 100° C.

(1) reagent: HCN+HCl, catalyst: $AlCl_3$ or $ZnCl_2$, solvent: $CHCl_3$ or $CH_2Cl_2$, condition: the reaction is carried out under cooling with ice, followed by hydrolysis with a dilute alkali, (2) reagent: CO+HCl, catalyst: $CuCl+AlCl_3$, solvent: benzene, condition: room temperature, (3) reagent: $DMF+POCl_3$, solvent: DMF, condition: under cooling with ice.

The oxidation of Step III is carried out by using a reagent such as potassium permanganate ($KMnO_4$) or chromium trioxide and a solvent such as water or acetic acid, preferably at a temperature from room temperature to about 100° C.

Preparation Process 3

The compound represented by the general formula (I) wherein R is OH, X is $$-\overset{CH_3}{\underset{|}{C}}=CH-$$

and n is 1 can be prepared by the following procedure.

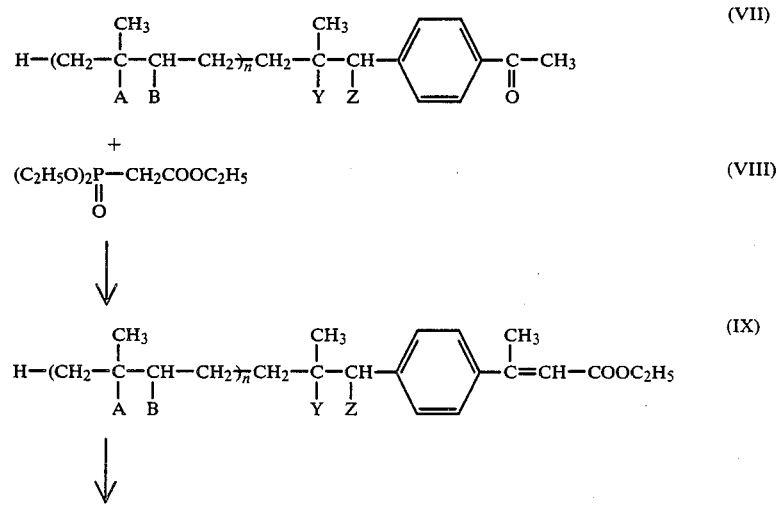

$$\underset{A\ B}{H-(CH_2-\overset{CH_3}{\underset{|}{C}}-CH-CH_2)_n} CH_2-\underset{Y\ Z}{\overset{CH_3}{\underset{|}{C}}-CH} -\underset{}{\underset{}{\bigcirc}}-\overset{CH_3}{\underset{|}{C}}=CH-COOH \quad (I''')$$

A compound (VII) is reacted with a compound (VIII) in the presence of a base such as sodium methylate, sodium ethylate, t-BuOK or NaH in a solvent such as tetrahydrofuran, ether DMF, benzene or hexane at a temperature of 0° to 80° C. to obtain an ester (IX). The ester (IX) is hydrolyzed or reduced by an ordinary method to obtain a compound (I''') which is one of the objective compounds. The starting material (VII) can be prepared, for example, by the following methods which will be shown schematically below.

(Method 1)

Y—⌬—COOH (X)    Y—⌬—COCl (XI)

\+                 +

MeLi.ether solution    MeMgBr.ether solution
room temp. (XII)          (XIII)
                          −70∼0° C.

↓

(VII)

wherein Y is a group represented by the formula $$H-(CH_2-\overset{CH_3}{\underset{\underset{A}{|}}{C}}-\underset{B}{CH}-CH_2)_n CH_2-\overset{CH_3}{\underset{\underset{Y}{|}}{C}}-\underset{Z}{CH}-$$

(A, B, Y and Z are as defined above)

(Method 2)

Y—⌬ + CH₃COCl ⟹ (VII)
(XIV)     (XV)

This reaction is carried out in the presence of a catalyst such as AlCl₃, SnCl₄ or ZnCl₂ in a solvent such as CCl₄, CH₂Cl₂ or benzene at a temperature of ice cooling to 80° C.

(Method 3)

(Step I)

CH₃—⌬—C(=O)—CH₃ + ethylene glycol $\xrightarrow[\text{P—toluene-sulfonic acid}]{\text{azeotropic dehydtation}}$
(XVI)             solvent: benzene -continued
(Method 3)

CH₃—⌬—C(CH₃)(O—CH₂—CH₂—O)

(XVII)

(Step II)

(VII) + NBS $\xrightarrow[\text{reflux}]{\text{benzoyl peroxide}}$ solvent: CCl₄ or benzene BrCH₂—⌬—C(CH₃)(O—CH₂—CH₂—O)

(XVIII)

(Step III)

(XVII) + (C₆H₅)₃P $\xrightarrow[\text{solvent: benzene or toluene}]{\text{reflux}}$ (XIX)

(C₂H₅)₃P⁺CH₂—⌬—C(CH₃)(O—CH₂—CH₂—O) Br⁻

(XX)

(Step IV)

(XX) + (CH₃)₂C=CH—CH₂—CH₂—C(CH₃)=O →

(XXI)

(CH₃)₂C=CH—CH₂—CH₂—C(CH₃)=CH—⌬—CH(CH₃)(O—O)

(XXII)

(Step V)

(XXII) $\xrightarrow[\text{solvent: alcohol or acetone}]{\text{HCl}}$ (VII)

The reaction of Step IV is carried out in the presence of a base such as sodium methylate, sodium ethylate, t-BuOK, MeLi, n-BuLi or C₆H₅Li in a solvent such as ethanol, methanol, tetrahydrofuran (THF), ether, DMF or DMSO, preferably at a reaction temperature a room temperature to about 100° C.

Preparation Process 4

The compound represented by the general formula (I) wherein R is OH, X is —CH₂—CH₂— and m is 1 can be prepared by the following procedure.

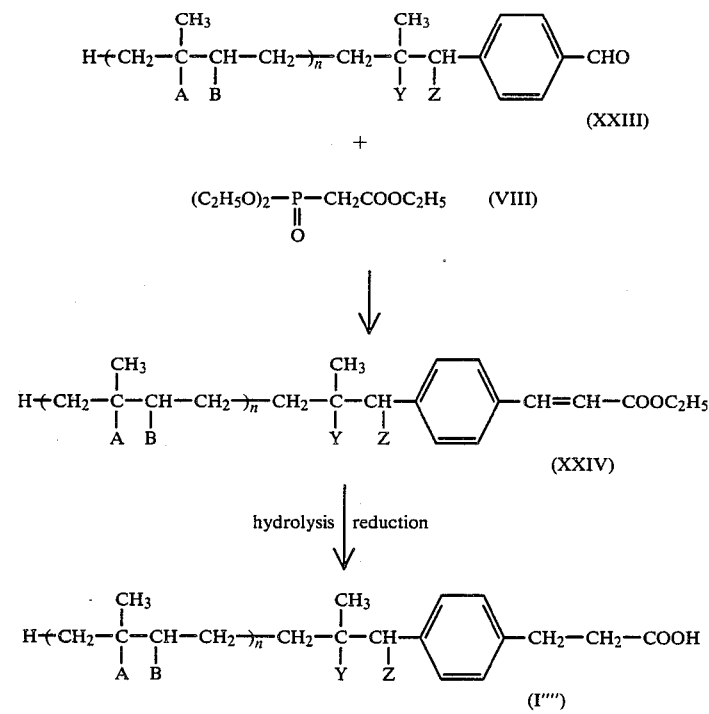

In Step 1, the preparation of the compound (XXIV) is carried out in the presence of a base such as sodium methylate, sodium ethylate, t-BuOK or NaH in a solvent such as tetrahydrofuran (THF), ether, DMF, benzene or hexane at a reaction temperature of 0° to 80° C.

The obtained compound (XXIV) is reduced and hydrolyzed by an ordinary method to obtain a compound (I'''') which is one of the objective compounds. The reduction is carried out in the presence of a catalyst such as Raney nickel, Pd-C, PtO₂ or Pt-C in a solvent such as ethanol, methanol, ethyl acetate, dioxane or acetic acid under a pressure of normal pressure to 150 kg/cm² at a temperaure of room temperature to about 100° C. If necessary, a small amount of acetic, hydrochloric or perchloric acid may be added as a co-catalyst. The addition of such a co-catalyst promotes the reaction or enables the reaction to proceed under more moderate conditions.

The hydrolysis is carried out in the presence of a base such as KOH or NaOH or an acid such as hydrochloric or sulfuric acid according to an ordinary method. In the hydrolysis, methanol, ethanol, propanol, ethylene glycol or propylene glycol is used as a solvent, while the reaction temperature may be about room temperature.

The starting material (XXIII) can be prepared, for example, by the following procedure which will be described schematically.

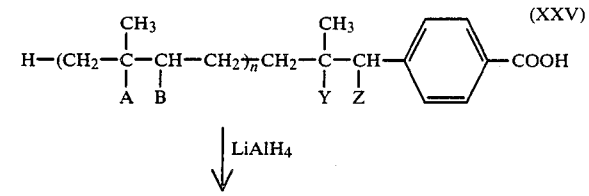

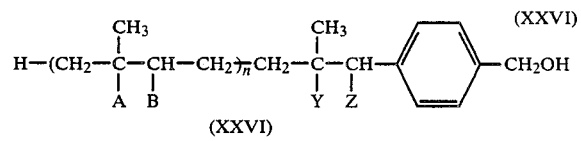

Preparation Process 5

The compound represented by the general formula (I) wherein R is OH, X is —CH₂— and m is 1 can be prepared by the following procedure.

(Method 1)

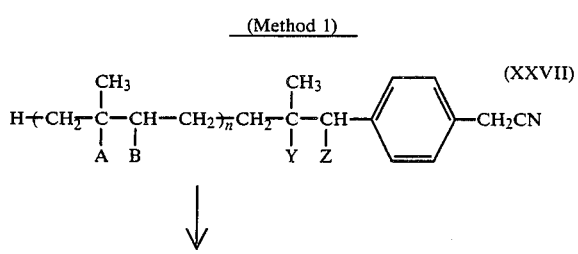

-continued
(Method 1)

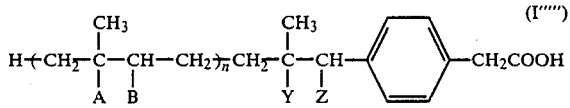
(I'''')

The compound (XXVI) is hydrolyzed in the presence of KOH, NaOH or the like according to an ordinary method to obtain the carboxylic acid (I'''') which is one of the objective compounds. This hydrolysis is preferably carried out in a solvent such as propylene glycol or ethylene glycol at a temperature of 80° to 150° C.

The starting compound (XXVI) can be prepared, for example, by the following procedure, the reaction formula of which will be shown below.

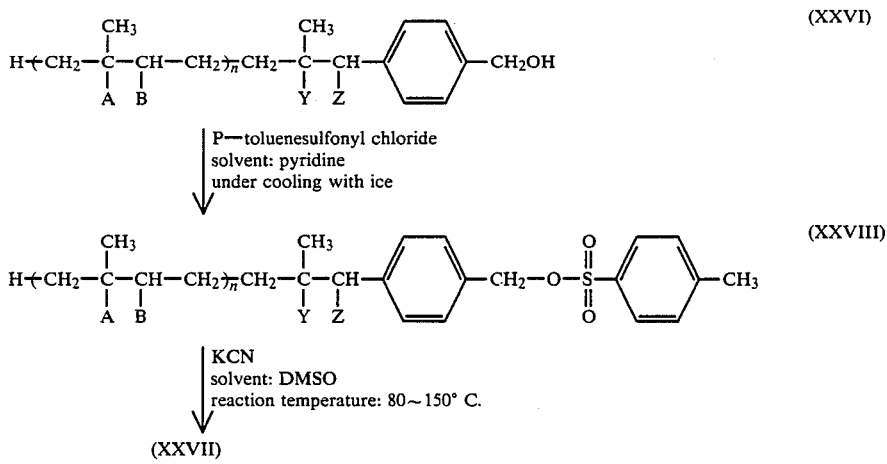

(XXVI)

P—toluenesulfonyl chloride
solvent: pyridine
under cooling with ice (XXVIII)

KCN
solvent: DMSO
reaction temperature: 80~150° C.

(XXVII)

(Method 2)

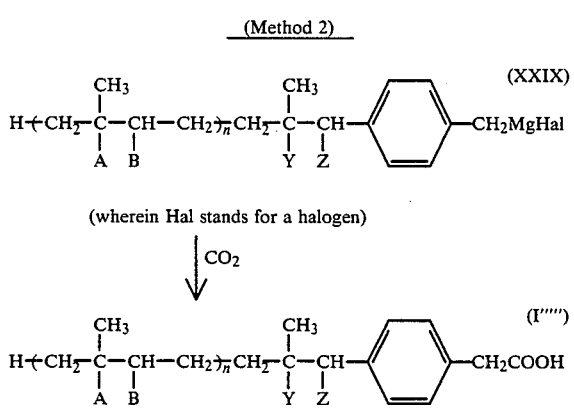
(XXIX)

(wherein Hal stands for a halogen)

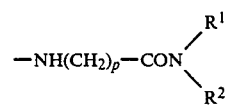

(I''''')

The compound (XXIX) is reacted with carbon dioxide by an ordinary method (Grignard reaction) to obtain the carboxylic acid (I''''') which is one of the objective compounds. The reaction temperature is from −70° C. to room temperature.

The starting compound (XXIX) can be prepared, for example, by the following procedure, the reaction formula of which will be shown below.

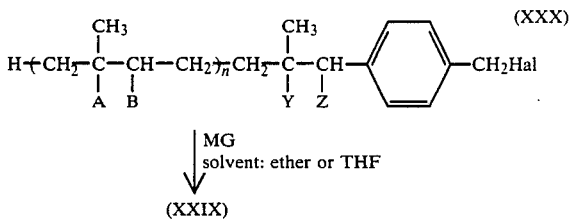
(XXX)

MG
solvent: ether or THF (XXIX)

Preparation Process 6

The compound represented by the general formula (I) wherein R is not a hydroxyl group, but a group represented by the formula $$-NH(CH_2)_p-CON\begin{matrix}R^1\\R^2\end{matrix}$$

(wherein p, $R^1$ and $R^2$ are as defined above), —NH—$(CH_2)_q$—OH (wherein q is as defined above) or $$-NH-CH_2-\underset{\underset{OH}{|}}{CH}-CH_2OH$$

can be prepared by reacting the carboxylic acid prepared by the above process with a reactive acid derivative such as an acid halide and reacting the resulting compound with an amine to obtain the corresponding amide.

(Method 1)

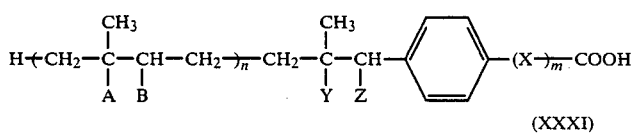
(XXXI)

(Method 1)

(wherein, n, m, A, B, Y and Z are as defined above)

[Step 1]

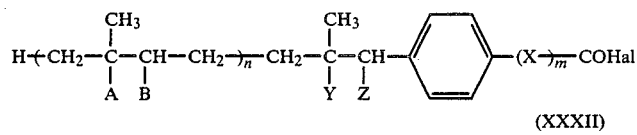

(XXXII)

(wherein Hal stands for a halogen atom)

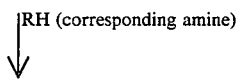

[Step 2]

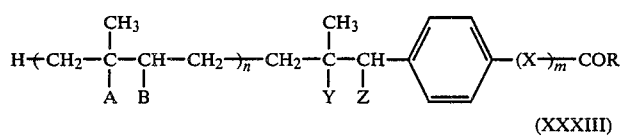

(XXXIII)

(wherein R is as defined above)

In Step 1, the carboxylic acid is converted into the corresponding acid halide. For example, the acid is reacted with $SOCl_2$, $SO_2Cl_2$, $POCl_3$, $PCl_5$, $PCl_3$ or oxalyl chloride into the acid chloride. This reaction may be carried out without any solvent or in a solvent such as benzene or toluene under reflux.

In Step 2, the acid halide obtained in Step 1 is reacted with the corresponding amine RH according to an ordinary process to obtain an objective acid amide (XXXIII).

Examples of the RH include

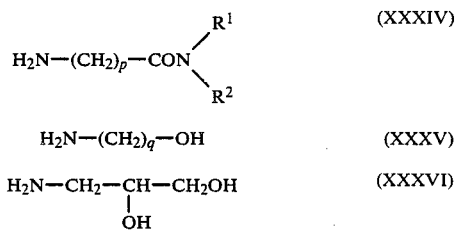

wherein p, $R^1$, $R^2$ and q are as defined above.

This reaction is carried out in a solvent such as tetrahydrofuran, ether, benzene, chloroform or toluene, generally in the presence of a base such as pyridine, triethylamine or potassium carbonate.

(Method 2)

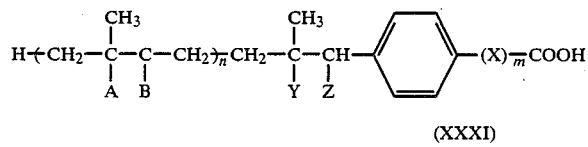

(XXXI)

[Step 1]

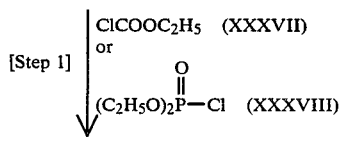

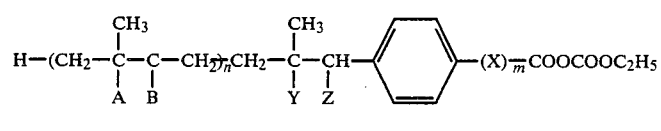

(XXXIX)

or (Method 2)

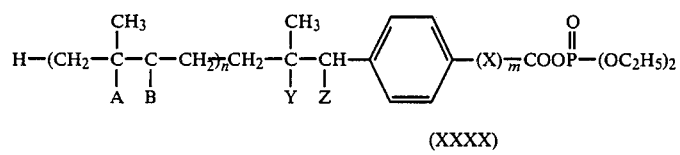

(XXXX)

[Step 2] ↓ RH (corresponding amide)

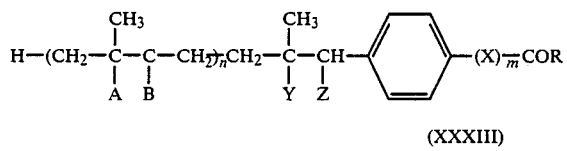

(XXXIII)

In Step 1, the carboxylic acid (XXXI) is condensed with the compound (XXXVII) or (XXXVIII) to obtain the compound (XXXIX) or (XXXX). This condensation is carried out in a solvent such as tetrahydrofuran, ether, benzene or chloroform, generally in the presence of a base such as triethylamine or pyridine. The preferred reaction temperature is from $-50°$ C. to a room temperature.

In Step 2, the compound (XXXIX) or (XXXX) obtained in Step 1 is reacted with the corresponding amine [(XXXXIV). (XXXV) or (XXXVI)] by an ordinary method to obtain an objective amide (XXXIII).

This reaction is carried out generally in the presence of a base such as triethylamine or pyridine.

The effect of the compound according to the present invention will be described in further detail by the pharmacological animal experiment.

Experimental Example

Antihypercholesterolemic activity

Method

A male SD rat of 4 weeks of age was fed with a high cholesterolemic bait for 3 days, followed by returning to a normal bait. The test compound which will be described below was orally administered to the rat twice a day for 2 days. 2 days after returning to a normal bait, blood was drawn from the rat and examined for the total amount of serum cholesterol. Clofibrate was used as a control midicine. The control group exhibited an average cholesterol value of 130 mg/dl. The rates of the decrease in cholesterol value with respect to the test compound are shown in Table 1.

The test compound was emulsified with 1% Tween 80 and administered in an amount of 50 mg per kg of weight.

| Test compound | |
|---|---|
| compound A: | 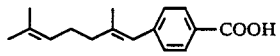 |
| compound B: | 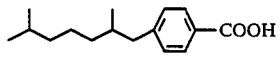 |
| compound C: | 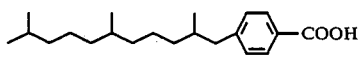 |
| compound D: | 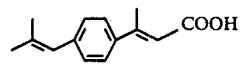 |
| compound E: | 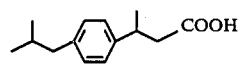 |
| compound F: | 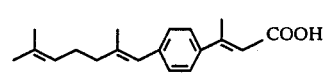 |
| compound G: | 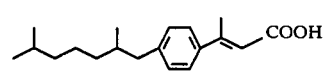 |
| compound H: | 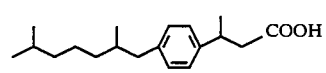 |
| compound I: | 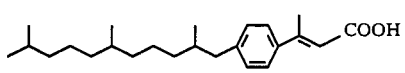 |
| compound J: | 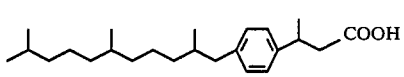 |
| compound K: | 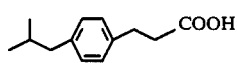 |
| compound L: | 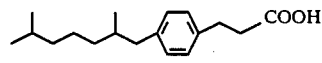 |
| compound M: | 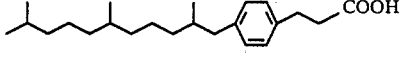 |
| compound N: | 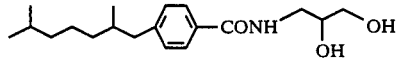 |
| compound O: | 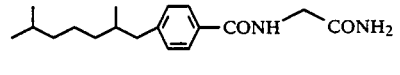 |
| compound P: | 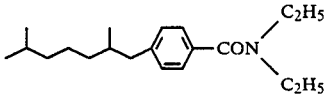 |

| Test compound | |
|---|---|
| compound Q: | 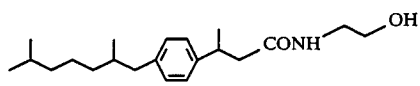 |
| compound R: | 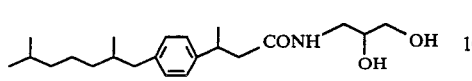 |
| compound S: | 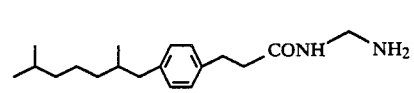 |
| compound T: | 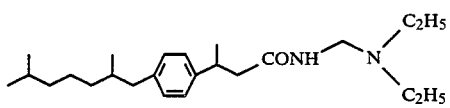 |
| compound U: | 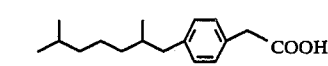 |
| compound V: | 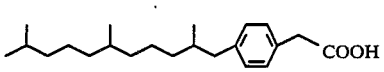 |

TABLE 1

| Test compound | Rate of the decrease in cholesterol value | Test compound | Rate of the decrease in cholesterol value |
|---|---|---|---|
| compound A | 19 | compound M | 25 |
| compound B | 21 | compound N | 18 |
| compound C | 28 | compound O | 18 |
| compound D | 20 | compound P | 17 |
| compound E | 21 | compound Q | 32 |
| compound F | 25 | compound R | 25 |
| compound G | 28 | compound S | 26 |
| compound H | 29 | compound T | 24 |
| compound I | 28 | compound U | 20 |
| compound J | 27 | compound V | 21 |
| compound K | 18 | clofibrate | 18 |
| compound L | 26 | | |

It is apparent from the above pharmacological experiment that the compound of the present invention has an excellent antihypercholesterolemic activity. Therefore, it is useful as a medicine based on the antihypercholesterolemic activity, particularly as an antihypercholesterolemic agent or an antiarteriosclerotic agent.

Further, though an antihypercholesterolemic agent must be administered for a long period because of the nature of the disease, the compound of the present invention exhibits a very low toxicity and is a very safe compound, so that the present invention is very valuable in this respect. With respect to the toxicity of the compound according to the present invention, when the above described compounds A to V were administered to SD rats (of a weight of about 200 g), neither death nor adverse reactions were observed.

The dosage of the compound of the present invention to be administered to a patient as an antihypercholesterolemic agent or an antiarteriosclerotic agent is remarkably varied depending upon the kind of patient, the degree of the disease, the kind of compound or the age of patient and not particularly limited. The compound of the present invention is administered orally or parenterally in a dosage of about 10 to 1000 mg, preferably about 30 to 300 mg, per adult by two to four portions a day. The form of the compound to be administered may be powder, fine granule, granule, pellet, capsule, injection or the like. The formulation is carried out by using an ordinary formulating carrier and according to an ordinary method.

The solid medicine for oral administration can be formulated by adding a filler, if necessary, together with binder, disintegrating agent, lubricant, coloring matter or corrigent, to a principal agent and converting the obtained mixture into pellet, coated pellet, granule, powder or capsule according to an ordinary method.

Examples of the filler include lactose, corn starch, sucrose, glucose, sorbitol, crystalline cellulose and silicon dioxide. Examples of the binder include polyvinyl alcohol, polyvinyl ether, ethylcellulose, methylcellulose, gum arabic, tragacanth, gelatin, shellac, hydroxypropylcellulose, hydroxypropylstarch and polyvinylpyrrolidone. Examples of the disintegrating agent include starch, agar, gelatin powder, crystalline cellulose, calcium carbonate, sodium hydrogen carbonate, calcium citrate, dextrin and pectin. Examples of the lubricant include stearic acid, magnesium, talc, polyethylene glycol, silica and hardened vegetable oil. The coloring matter may be any one which is permitted to be added to medicines. Examples of the corrigent include cocoa powder, menthol, aromatic acid, metha oil, borneol and powdered cinnamon bark. Of course, the pellet or granule may be coated with sugar, gelatin or the like.

In the preparationn of an injection, a principal agent is, if necessary after the addition of a pH adjuster, buffer, stabilizer, solubilizing agent or the like, converted into a subcutaneous, intramuscular or intravenous injection.

Now, the following Formulation Example will describe the case where N-[4-(2′,6′-dimethylheptyl]-N′,N′-diethylglycinamide, which is one of the representative compounds of the present invention, (hereinafter referred to as "principal agent") is used as an active ingredient.

| Formulation Example (pellet) | |
|---|---|
| principal agent | 10 g |
| anhydrous silicic acid | 50 g |
| crystalline cellulose | 70 g |
| corn starch | 36 g |
| hydroxypropylcellulose | 10 g |
| magnesium stearate | 4 g |

The mixture of the above formulation was treated according to an ordinary procedure to obtain a pellet having a pellet weight of 180 mg.

Now, Examples of the present invention will be described, though the present invention is not limited to them.

EXAMPLE 1

4-(1′-Isobutenyl)benzoic acid

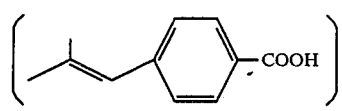

(1) Synthesis of methyl 4-bromomethylbenzoate 15 g of methyl toluate, 17.8 g of N-bromosuccinimide and 0.5 g of benzoyl peroxide were suspended in 50 ml of carbon tetrachloride under stirring. The suspension was heated under reflux for 30 minutes. After the completion of the reaction, the reaction mixture was washed with water, concentrated and distilled under a reduced pressure to obtain 18.5 g of the title compound (yield: 81%).

(2) Diethyl (4-methoxycarbonylphenyl)methylphosphonate 22.9 g of methyl 4-bromomethylbenzoate obtained in the above step (1) was reacted with 16.6 g of triethyl phosphite at 120° C. for 2 hours. After the completion of the reaction, the reaction mixture was distilled under a reduced pressure to obtain 23.2 g of the title compound (yield: 82%).

(3) 4-(1'-isobutenyl)benzoic acid 2.8 g of sodium hydride was suspended in 50 ml of DMF. 37 g of diethyl (4-methoxycarbonylphenyl)methylphosphate was dropwise added to the suspension, followed by the addition of 20 ml of acetone. The mixture was reacted at 50° C. for 2 hours. The reaction mixture was poured into water and extracted with hexane. The extract was washed with water and concentrated. The residue was dissolved in ethanol and 15 g of potassium hydroxide was added to the solution, followed by dissolution. The resulting solution was heated under reflux for one hour.

The reaction mixture was neutralized with dilute hydrochloric acid and extracted with ether. The extract was washed with water and concentrated. The residue was recrystallized from benzene to obtain 7.9 g of the objective compound as a white crysal (yield: 42%).

| Elemental analysis as $C_{11}H_{12}O_2$ | | |
|---|---|---|
| | C | H |
| calculated (%) | 74.97 | 6.86 |
| observed (%) | 75.15 | 7.04 |

Mass(m/z): 176(M+).
$^1$H-NMR(DMSO-$d_6$): δ1.90(3H, d, J=4), 1.92(3H, d, J=4), 6.28(1H, br.s), 7.28(2H, d, J=9), 7.97(2H, d, J=9).

EXAMPLE 2

4-Isobutylbenzoic acid

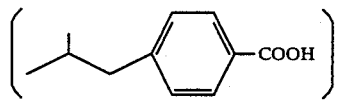

17.6 g of 4-(1'-isobutenyl)benzoic acid was dissolved in ethanol and catalytically reduced in the presence of Raney nickel catalyst.

After the removal of the catalyst by filtration, the reaction mixture was concentrated and recrystallized from hexane to obtain 16.9 g of the objective compound as a white crystal (yield: 95%).

| Elemental analysis as $C_{11}H_{14}O_2$ | | |
|---|---|---|
| | C | H |
| calculated (%) | 74.13 | 7.92 |
| observed (%) | 74.30 | 8.01 |

Mass(m/z): 178(M+).

$^1$H-NMR-(DMSO-$d_6$): δ0.89(6H, d, J=8), 1.7–2.1(1H), 2.52(2H, d, J=8), 7.20(2H, d, J=9), 7.97(2H, d, J=9).

EXAMPLE 3

4-(2',6'-Dimethyl-1',5'-heptadienyl)benzoic acid

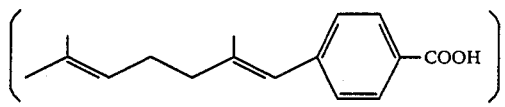

6.5 g of sodium methylate was dissolved in 50 ml of DMF. 37 g of diethyl (4-methoxycarbonylphenyl)methylphosphonate was dropwise added to the solution.

12.6 g of 6-methyl-5-hepten-2-one was added to the resulting mixture to carry out the reaction at 50° C. for 2 hours. The reaction mixture was treated according to the same procedure as the one described in Example 1 to obtain 15.3 g of the objective compound as a white crystal (yield: 63%).

| Elemental analysis as $C_{16}H_{20}O_2$ | | |
|---|---|---|
| | C | H |
| calculated (%) | 78.65 | 8.25 |
| observed (%) | 78.89 | 8.46 |

Mass(m/z): 244(M+).
$^1$H-NMR (CDCl$_3$): δ1.5–1.8(6H), 1.8–1.9(3H), 1.9–2.3(4H), 4.9–5.3(1H), 6.3(1H, br. s), 7.15–7.4(2H, m), 7.98(2H, d, J=9).

EXAMPLE 4

4-(2',6'-Dimethylheptyl)benzoic acid

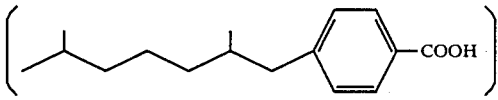

24.4 g of 4-(2',6'-dimethyl-1',5'-heptadienyl)benzoic acid obtained in Example 3 was treated according to the same procedure as the one described in Example 2 to obtain 20.6 g of the objective compound as a white crystal (yield: 83%).

| Elemental analysis as $C_{16}H_{24}O_2$ | | |
|---|---|---|
| | C | H |
| calculated (%) | 77.37 | 9.74 |
| observed (%) | 77.39 | 9.88 |

Mass(m/z): 248(M+).
$^1$H-NMR (CDCl$_3$): δ0.84(3H, d, J=7), 0.86(6H, d, J=7), 1.0–1.9(8H), 2.2–2.9(2H, m), 7.20(2H, d, J=9), 7.97(2H, d, J=9).

EXAMPLE 5

4-(2',6',10'-Trimethylundecyl)benzoic acid

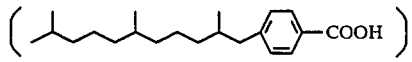

8.2 of sodium ethylate was dissolved in 50 ml of DMF, followed by the dropwise addition of 37 g of diethyl (4-methoxycarbonylphenyl)methylphosphonate. 19.4 g of geranylacetone was added to the resulting mixture to carry out the reaction at 50° C. for 2 hours.

The reaction mixture was treated according to the same procedure as the one described in Example 1 or 2 and purified by silica gel chromatography to obtain 26.7 g of the objective compound as a waxy solid (yield: 84%).

| Elemental analysis as $C_{21}H_{34}O_2$ | | |
|---|---|---|
|  | C | H |
| calculated (%) | 79.19 | 10.76 |
| observed (%) | 79.25 | 10.89 |

Mass (m/z): 318(M+).

$^1$H-NMR(CDCl$_3$): δ0.84(3H, d, J=7), 0.86(9H, d, J=7), 1.0–1.9(15H), 2.2–2.9(2H, m), 7.20(2H, d, J=9), 7.98(2H, d, J=9).

EXAMPLE 6

3-[4'-(1''-Isobutenyl)phenyl]-2-butenoic acid

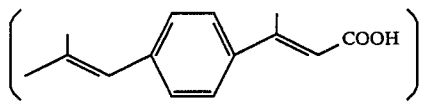

8.8 g of 4-(1'isobutenyl)benzoic acid was dissolved in ether. The resulting solution was dropwise added to 500 ml of a 1.4M solution of methyllithium in ether. The reaction mixture was poured into ice, washed with water and concentrated.

1.2 g of sodium hydride was suspended in 30 ml of THF, followed by the dropwise addition of 12.0 g of diethyl ethoxycarbonylmethylphosphonate. The above concentration residue was dropwise added to the obtained mixture to carry out the reaction at 50° C. for 2 hours. The reaction mixture was washed with water, concentrated and dissolved in ethanol. 7 g of potassium hydroxide was added to the obtained solution, followed by dissolution.

The obtained solution was poured into dilute hydrochloric acid and extracted with ether. The extract was washed with water and concentrated. The residue was recrystallized from hexane to obtain 3.0 g of the objective compound as a white crystal (yield: 28%).

| Elemental analysis as $C_{14}H_{16}O_2$ | | |
|---|---|---|
|  | C | H |
| calculated (%) | 77.75 | 7.46 |
| observed (%) | 77.83 | 7.66 |

Mass (m/z): 216(M+).

$^1$H-NMR(CDCl$_3$): δ1.89(3H, d, J=4), 1.91(3H, d, J=4), 2.5–2.6(3H), 6.1–6.2(1H), 6.2–6.3(1H, br.s), 7.1–7.6(4H, m).

EXAMPLE 7

3-(4'-Isobutylphenyl)-2-butenoic acid

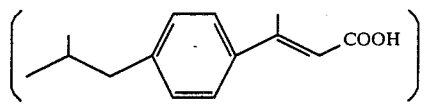

19.7 g of 4-isobutylbenzoyl chloride was dissolved in ether, followed by the dropwise addition of 33 ml of 3M solution of methylmagnesium iodide in ether at −40° C. Water was added to the mixture to carry out the decomposition and the resulting mixture was washed with water and concentrated.

6.5 g of sodium methylate was suspended in 50 ml of THF, followed by the dropwise addition of 30 g of diethyl ethoxycarbonylmethylphosphonate. The above concentration residue was dropwise added to the obtained mixture to carry out the reaction at 50° C. for 2 hours. The reaction mixture was washed with water, concentrated and dissolved in ethanol. 17 g of potassium hydroxide was added to the obtained solution, followed by dissolution.

The obtained solution was poured into dilute hydrochloric acid and extracted with ether. The extract was washed with water and concentrated. The residue was recrystallized from hexane to obtain 10.2 g of the objective compound as a white crystal (yield: 47%).

| Elemental analysis as $C_{14}H_{18}O_2$ | | |
|---|---|---|
|  | C | H |
| calculated (%) | 77.03 | 8.31 |
| observed (%) | 77.17 | 8.48 |

Mass(m/z): 218(M+).

$^1$H-NMR(CDCl$_3$): δ0.90(6H, d, J=8), 1.7–2.1(1H), 2.51(2H, d, J=8), 2.55–2.6(3H), 6.1–6.2(1H), 7.16(2H, d, J=9), 7.42(2H, d, J=9).

EXAMPLE 8

3-(4'-Isobutylphenyl)butyric acid

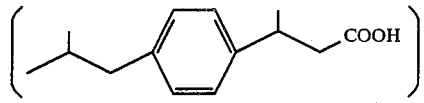

21.8 g of 3-(4'-isobutylphenyl)-2-butenoic acid was treated according to the same procedure as the one described in Example 2 to obtain 18.3 g of the objective compound as a white crystal (yield: 83%).

| Elemental analysis as $C_{14}H_{20}O_2$ | | |
|---|---|---|
|  | C | H |
| calculated (%) | 76.32 | 9.15 |
| observed (%) | 76.54 | 9.39 |

Mass(m/z): 220(M+).

$^1$H-NMR(CDCl$_3$): δ0.89(6H, d, J=8), 1.28(3H, d, J=8), 1.7–2.1(1H), 2.51(2H, d, J=8), 2.5–2.7(2H), 3.0–3.1(1H), 7.0–7.2(4H).

EXAMPLE 9

3-[4'-(2'',6''-Dimethyl-1'',5''-heptadienyl)phenyl]-2-butanoic acid

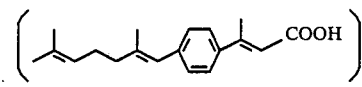

26.3 g of 4-(2',6'-dimethyl-1',5'-heptadienyl)benzoyl chloride was treated according to the same procedure as the one described in Example 7 to obtain 14.7 g of the objective compound as a white crystal (yield: 52%).

| Elemental analysis as $C_{19}H_{24}O_2$ | | |
| --- | --- | --- |
|  | C | H |
| calculated (%) | 80.24 | 8.51 |
| observed (%) | 80.31 | 8.67 |

Mass (m/z): 284(M+).
$^1$H-NMR(CDCl$_3$): δ1.64(3H, s), 1.71(3H, s), 1.9–2.0(3H), 2.1–2.3(4H), 2.5–2.6(3H), 5.0–5.3(1H), 6.1–6.2(1H), 6.2–6.3(1H), 7.1–7.6(4H).

EXAMPLE 10

3-[4'-(2'',6''-Dimethylheptyl)phenyl]-2-butenoic acid

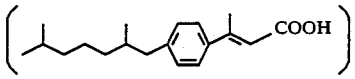

12.4 g of 4-(2',6'-dimethylheptyl)benzoic acid was treated according to the same procedure as the one described in Example 6 and purified by chromatography to obtain 6.0 g of the objective compound as a wax (yield: 42%).

| Elemental analysis as $C_{19}H_{28}O_2$ | | |
| --- | --- | --- |
|  | C | H |
| calculated (%) | 79.12 | 9.79 |
| observed (%) | 79.03 | 9.84 |

Mass(m/z): 288(M+).
$^1$H-NMR(CDCl$_3$): δ0.84(3H, d, J=7), 0.87(6H, d, J=7), 0.9–1.9(8), 2.2–2.8(5H), 6.1–6.2(1H), 7.16(2H, d, J=9), 7.42(2H, d, J=9).

EXAMPLE 11

3-[4'-(2'',6''-Dimethylheptyl)phenyl]acetic acid

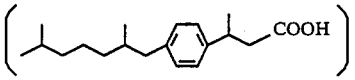

This compound can be prepared by any of the following three methods.

(Method 1)

28.8 g of 3-[4'-(2'',6''-dimethylheptyl)phenyl]-2-butenoic acid was treated according to the same procedure as the one described in Example 2 and purified by silica gel chromatography to obtain 25.2 g of the objective compound as a colorless oil (yield: 87%).

| Elemental analysis as $C_{19}H_{30}O_2$ | | |
| --- | --- | --- |
|  | C | H |
| calculated (%) | 78.57 | 10.41 |
| observed (%) | 78.71 | 10.57 |

Mass(m/z): 290(M+).
$^1$H-NMR(CDCl$_3$): δ0.84(3H, d, J=7), 0.86(6H, d, J=7), 0.9–1.9(8H), 1.28(3H, d, J=8), 2.1–2.8(4H, m), 3.0–3.4(1H, m), 7.0–7.2(4H).

(Method 2) 13.4 g of 4-methylacetophenone was dissolved in 100 ml of benzene, followed by the addition of 20 ml of ethylene glycol and a catalytic amount of p-toluenesulfonic acid. The mixture was azeotropically dehydrated for several hours, cooled and washed by pouring it into an aqueous solution of sodium hydrogen carbonate. The product was washed with water and dried.

17.8 g of N-bromosuccinimide and 0.2 g of benzoyl peroxide were added to the obtained product and the resulting mixture was heated under reflux, cooled, washed with water and concentrated.

28.8 g of triphenylphosphine and the concentration residue were dissolved in 200 ml of benzene. The obtained solution was heated under reflux and cooled. The precipitate was filtered, washed with water and dried.

The obtained powder was suspended in 200 ml of DMF, followed by the dropwise addition of a solution of 6.8 g of sodium ethylate in DMF. 12.0 g of 6-methyl-5-hepten-2-one was dropwise added to the resulting mixture to carry out the reaction at 50° C. for 2 hours. The reaction mixture was poured into water, extracted with hexane, washed with water and concentrated.

The residue was dissolved in methanol. Hydrochloric acid was added to the obtained solution to carry out the reaction at 50° C. for one hour. The reaction mixture was poured into water, neutralized with an aqueous solution of sodium hydrogen carbonate, extracted with hexane, washed with water and concentrated.

1.2 g of sodium hydride was suspended in 50 ml of THF, followed by the dropwise addition of 12.0 g of diethyl ethoxycarbonylmethylphosphonate. The concentration residue was dropwise added to the obtained mixture to carry out the reaction at 50° C. for 2 hours. The reaction mixture was poured into water, extracted with hexane, washed with water and concentrated.

The residue was dissolved in ethanol and catalytically reduced in the presence of Raney nickel catalyst. After the removal of the catalyst by filtration, 7 g of potassium hydroxide was dissolved in the obtained solution. The obtained mixture was poured into dilute hydrochloric acid, extracted with ether, washed with water, concentrated and purified by column chromatography to obtain 3.3 g of the objective compound (yield: 11%).

(Method 3)

38.9 of benzyltriphenylphosphonium chloride was suspended in 200 ml of DMF, followed by the dropwise addition of 6.8 g of sodium ethylate in DMF. 12.0 g of 6-methyl-5-hepten-2-one was dropwise added to the obtained mixture to carry out the reaction at 50° C. for 2 hours. The reaction mixture was poured into water, extracted with hexane, washed with water and concentrated.

The residue was dissolved in ethanol, catalytically reduced in the presence of Raney nickel catalyst, filtered to remove the catalyst and concentrated.

20.0 g of anhydrous aluminum chloride powder was suspended in 100 ml of carbon tetrachloride, followed by the addition of 11.8 g of acetyl chloride under cooling. The concentration residue was dropwise added to the obtained mixture under cooling with ice to carry out the reaction for one hour. The reaction mixture was poured into ice-water. The organic layer was washed with dilute hydrochloric acid, aqueous solution of sodium hydrogen carbonate and water and concentrated.

1.2 g of sodium hydride was suspended in 50 ml of THF, followed by the dropwise addition of 12.0 g of diethyl ethoxycarbonylmethylphosphonate. The concentration residue was dropwise added to the obtained mixture to carry out the reaction at 50° C. for 2 hours. The reaction mixture was poured into water, extracted with hexane, washed with water and concentrated.

The residue was dissolved in ethanol, catalytically reduced in the presence of Raney nickel catalyst and filtered to remove the catalyst. 7 g of potassium hydroxide was dissolved in the obtained solution. The resulting solution was poured into dilute hydrochloric acid, extracted with ether, washed with water, concentrated and purified by column chromatography to obtain 9.9 g of the objective compound (34%).

EXAMPLE 12

3-[4'-(2'',6'',10''-Trimethylundecyl)phenyl]-2-butenoic acid

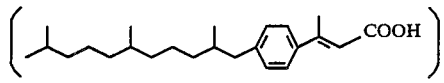

15.9 g of 4-(2',6',10'-trimethylundecyl)benzoic acid was treated according to the same procedure as the one described in Example 6 and purified by silica gel chromatography to obtain 9.8 g of the objective compound as a wax (yield: 55%).

| Elemental analysis as $C_{24}H_{38}O_2$ | | |
|---|---|---|
| | C | H |
| calculated (%) | 80.39 | 10.68 |
| observed (%) | 80.55 | 10.73 |

Mass(m/z): 358(M+).
$^1$H-NMR(CDCl$_3$): δ0.84(3H, d, J=7), 0.87(9H, d, J=7), 0.9-1.9(15H), 2.2-2.8(5H), 6.1-6.2(1H), 7.15(2H, d, J=9), 7.42(2H, d, J=9).

EXAMPLE 13

3'[4'-(2'',6'',10''-Trimethylundecyl)phenyl]-butyric acid

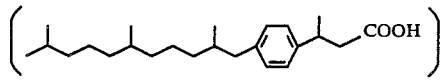

35.8 g of 3-[4'-(2'',6'',10''-trimethylundecyl)phenyl]-2-butenoic acid was treated according to the same procedure as the one described in Example 2 and purified by silica gel chromatography to obtain 32.4 g of the objective compound as a colorless oil (yield: 91%).

| Elemental analysis as $C_{24}H_{40}O_2$ | | |
|---|---|---|
| | C | H |
| calculated (%) | 79.94 | 11.18 |
| observed (%) | 80.10 | 11.23 |

Mass(m/z): 360(M+).
$^1$H-NMR(CDCl$_3$): δ0.84(3H, d, J=7), 0.87(9H, d, J=7), 0.9-1.9(15H), 1.29(3H, d, J=8), 2.1-2.8(4H, m), 3.0-3.4(1H, m), 7.0-7.2(4H).

EXAMPLE 14

3-(4'-Isobutylphenyl)propionic acid

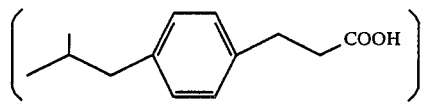

17.8 g of 4-isobutylbenzoic acid was reduced by the use of lithium aluminum hydride. The product was stirred in methylene chloride together with manganese dioxide. After 24 hours, the mixture was filtered and concentrated.

Separately, 2.4 g of sodium hydride was suspended in 30 ml of hexane, followed by the dropwise addition of 24 g of diethyl ethoxycarbonylphosphonate. The above concentration residue was dropwise added to the resulting mixture to carry out the reaction at 50° C. for 2 hours. After the completion of the reaction, the reaction mixture was washed with water, concentrated, dissolved in ethanol and catalytically reduced in the presence of Raney nickel catalyst. The reaction mixture was filtered to remove the catalyst and 10 g of potassium hydroxide was dissolved in the obtained filtrate.

The solution was poured into dilute hydrochloric acid, extracted with ether, washed with water and concentrated. The residue was purified by silica gel chromatography to obtain 11.7 g of the objective compound as a white powder (yield: 57%).

| Elemental analysis as $C_{13}H_{18}O_2$ | | |
|---|---|---|
| | C | H |
| calculated (%) | 75.69 | 8.80 |
| observed (%) | 75.84 | 8.89 |

Mass(m/z): 206(M+).
$^1$H-NMR(CDCl$_3$): δ0.89(6H, d, J=8), 1.7-2.1(1H), 2.4-3.2(4H), 2.51(2H, d, J=8), 7.0-7.2(4H).

EXAMPLE 15

3-[4'-(2'',6''-Dimethylheptyl)phenyl]propionic acid

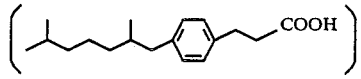

24.8 g of 4-(2',6'-dimethylheptyl)benzoic acid was used as a starting material and treated according to the same procedure as the one described in Example 14 to obtain 14.9 g of the objective compound as a white powder (yield: 54%).

| Elemental analysis as $C_{18}H_{28}O_2$ | | |
|---|---|---|
| | C | H |
| calculated (%) | 78.21 | 10.21 |
| observed (%) | 78.31 | 10.29 |

Mass(m/z): 276(M+).

$^1$H-NMR(CDCl$_3$): δ0.84(3H, d, J=7), 0.87(6H, d, J=7), 1.0-1.9(8H), 2.2-3.2(6H), 7.0-7.2(4H).

EXAMPLE 16

3-[4'-(2'',6'',10''-Trimethylundecyl)phenyl]propionic acid

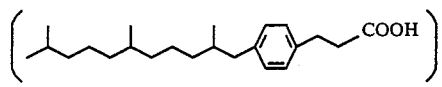

31.8 g of 4-(2',6',10'-trimethylundecyl)benzoic acid was used as a starting material and treated according to the same procedure as the one described in Example 14 to obtain 17.6 g of the objective compound as a wax (yield: 51%).

| Elemental analysis as $C_{23}H_{38}O_2$ | | |
|---|---|---|
| | C | H |
| calculated (%) | 79.71 | 11.05 |
| observed (%) | 79.95 | 11.23 |

Mass(m/z): 346(M+).

$^1$H-NMR(CDCl$_3$): δ0.80(3H, d, J=7), 0.84(9H, d, J=7), 1.0-1.9(15H, br.), 2.2-3.2(6H, m), 7.12(4H, s).

EXAMPLE 17

3'[4'-(2'',6''-Dimethylheptyl)benzoyl]amino-1,2-propanediol

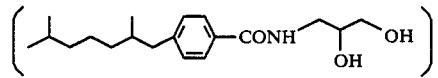

26.7 g of 4-(2',6'-dimethylheptyl)benzoyl chloride was dropwise added to a solution comprising 13.7 g of 3-amino-1,2-propanediol, 15 g of triethylamine and 100 ml of N,N-dimethylformamide under cooling with ice. After the completion of the reaction, the reaction mixture was poured into water, neutralized with dilute hydrochloric acid, and extracted with chloroform. The extract was washed with water, concentrated and purified by silica gel chromatography to obtain 20.2 g of the objective compound as a wax (yield: 63%).

| Elemental analysis as $C_{19}H_{31}NO_3$ | | |
|---|---|---|
| | C | H |
| calculated (%) | 70.99 | 9.72 |
| observed (%) | 80.25 | 9.95 |

Mass(m/z): 321(M+).

$^1$H-NMR(CDCl$_3$): δ0.84(3H, d, J=7), 0.86(6H, d, J=7), 1.0-1.9(8H), 2.2-2.8(2H), 3.2-3.7(5H), 3.7-4.0(2H), 6.9-7.1(1H), 7.19(2H, d, J=9), 7.96(2H, d, J=9).

EXAMPLE 18

N-[4-(2',6'-Dimethylheptyl)benzoyl]glycinamide

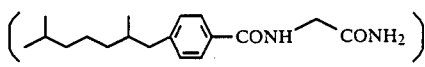

13.2 g of glycinamide hydrochloride was suspended in a mixture of 15 g of triethylamine and 100 ml of tetrahydrofuran. 26.7 g of 4-(2',6'-dimethylheptyl)benzoyl chloride was dropwise added to the suspension under cooling with ice.

The reaction mixture was poured into water and neutralized with dilute hydrochloric acid and extracted with ether. The extract was washed with water, concentrated and recrystallized from ethyl acetate to obtain 26.1 g of the objective compound as a white crystal (yield: 86%).

| Elemental analysis as $C_{18}H_{28}N_2O_2$ | | |
|---|---|---|
| | C | H |
| calculated (%) | 71.01 | 9.27 |
| observed (%) | 71.20 | 9.32 |

Mass(m/z): 304(M+).

$^1$H-NMR(CDCl$_3$): δ0.84(3H, d, J=7), 0.86(6H, d, J=7), 1.0-1.9(8H), 2.2-2.8(2H), 4.17(2H, d, J=4), 5.75-5.96(1H), 6.65-6.90(1H), 7.18(2H, d, J=9), 7.1-7.4(1H), 7.76(2H, d, J=9).

EXAMPLE 19

N-[4-(2',6'-Dimethylheptyl)benzoyl]-N',N'-diethylglycinamide

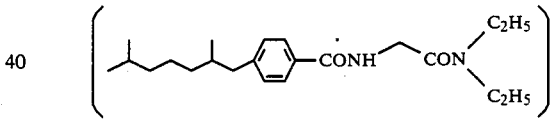

24.8 g of 4-(2',6'-dimethylheptyl)benzoic acid and 13.1 g of triethylamine were dissolved in 100 ml of tetrahydrofuran. 13.0 g of ethyl chlorocarbonate was dropwise added to the solution under cooling with ice.

20.9 g of ethylglycine hydrochloride was suspended in a mixture of 20.0 g of triethylamine and 100 ml of tetrahydrofuran. The above reaction mixture was added to the obtained suspension.

The reaction mixture was poured into water, neutralized with dilute hydrochloric acid and extracted with ether. The extract was washed with water, concentrated and dissolved in ethanol. 16 g of potassium hydroxide was added to the obtained solution, followed by dissolution.

The reaction mixture was poured into water, neutralized with dilute hydrochloric acid and extracted with ether. The extract was washed with water, concentrated and dissolved in a mixture of 15 g of triethylamine and 100 ml of tetrahydrofuran. 13.0 g of ethyl chlorocarbonate was dropwise added to the obtained solution, followed by the addition of 20 g of diethylamine.

The reaction mixture was poured into water, neutralized with dilute hydrochloric acid and extracted with ether. The extract was washed with water, concentrated and purified by silica gel column chromatography to obtain 11.5 g of the objective compound as a colorless oil (yield: 32%).

|  | Elemental analysis as $C_{22}H_{36}N_2O_2$ | |
|---|---|---|
|  | C | H |
| calculated (%) | 73.29 | 10.07 |
| observed (%) | 73.38 | 10.21 |

Mass(m/z): 360(M+).

$^1$H-NMR(CDCl$_3$): δ0.84(3H, d, J=7), 0.86(6H, d, J=7), 0.9-1.9(14H), 2.2-2.8(2H, m), 3.1-3.6(4H, m), 4.23(2H, d, J=4), 7.1-7.5(3H), 7.76(2H, d, J=9).

EXAMPLE 20

N-{3-[4'-(2",6"-Dimethylheptyl)phenyl]butanoyl}ethanolamine

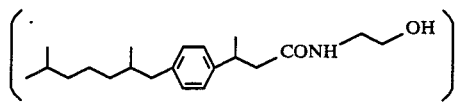

29.0 g of 3-[4'-(2",6"-dimethylheptyl)phenyl]butyric acid was dissolved in 10 ml of tetrahydrofuran. 25.3 g of triethylamine was added to the solution, followed by the dropwise addition of 13.0 g of ethyl chlorocarbonate under cooling with ice.

After the completion of the reaction, the reaction mixture was added to a solution of 9.0 g of ethanolamine in 100 ml of tetrahydrofuran at 0° C. or below.

The reaction mixture was poured into water, neutralized with dilute hydrochloric acid and extracted with ether. The extract was washed with water, concentrated and purified by silica gel column chromatography to obtain 29.1 g of the objective compound as a colorless oil (yield: 87.4%).

|  | Elemental analysis as $C_{21}H_{35}NO_2$ | |
|---|---|---|
|  | C | H |
| calculated (%) | 75.63 | 10.58 |
| observed (%) | 75.78 | 10.64 |

Mass(m/z): 333(M+).

$^1$H-NMR(CDCl$_3$): δ0.84(3H, d, J=7), 0.86(6H, d, J=7), 0.9-1.9(8H), 1.28(3H, d, J=8), 2.1-2.8(4H, m), 3.0-3.4(3H), 3.4-3.6(2H), 6.6-6.9(1H), 7.0-7.2(4H).

EXAMPLE 21

3-{3'-[4"-(2''',6'''-Dimethylheptyl)phenyl]butanoyl}aminino-1,2-propanediol

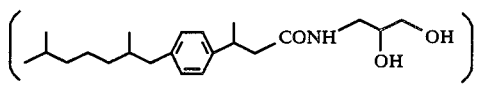

29.0 g of 3-[4'-(2",6"-dimethylheptyl)phenyl]butyric acid was used as a starting material and treated according to the same procedure as the one described in Example 17 to obtain 24.3 g of the objective compound as a wax (yield: 67%).

|  | Elemental analysis as $C_{22}H_{37}NO_3$ | |
|---|---|---|
|  | C | H |
| calculated (%) | 72.68 | 10.26 |
| observed (%) | 72.81 | 10.49 |

Mass(m/z): 363(M+).

$^1$H-NMR(CDCl$_3$): δ0.84(3H, d, J=7), 0.87(6H, d, J=7), 0.9-1.9(8H), 1.27(3H, d, J=8), 2.1-2.8(4H, m), 3.0-3.7(6H), 3.7-4.0(2H), 6.9-7.2(3H).

EXAMPLE 22

N-{3'[4'-(2",6"-Dimethylheptyl)phenyl]butanoyl} glycinamide

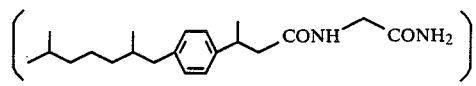

30.9 g of 3-[4'-(2",6"-dimethylheptyl)phenyl]butyryl chloride was used as a starting material, treated according to the same procedure as the one described in Example 18 and purified by silica gel chromatography to obtain 31.8 g of the objective compound as a white powder (yield: 92%).

|  | Elemental analysis as $C_{21}H_{34}N_2O_2$ | |
|---|---|---|
|  | C | H |
| calculated (%) | 72.79 | 9.89 |
| observed (%) | 72.84 | 9.97 |

Mass(m/z): 346(M+).

$^1$H-NMR(CDCl$_3$): δ0.84(3H, d, J=7), 0.86(6H, d, J=7), 0.9-1.9(8H), 1.28(3H, d, J=8), 2.1-2.8(4H, m), 3.0-3.4(1H, m), 4.18(2H, d, J=4), 5.57-5.95(1H), 6.65-6.90(1H), 7.0-7.4(5H).

EXAMPLE 23

N-{3-[4'-(2",6"-Dimethylheptyl)phenyl]butanoyl}-N',N'-diethylglycinamide

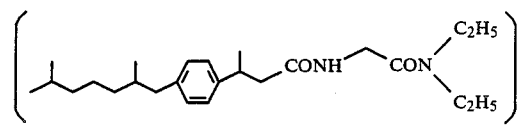

29.0 g of 3-[4'-(2',6'-dimethylheptyl)phenyl]butyric acid was used as a starting material and treated according to the same procedure as the one described in Example 19 to obtain 17.2 g of the objective compound as a colorless oil (yield: 42%).

|  | Elemental analysis as $C_{25}H_{42}N_2O_2$ | |
|---|---|---|
|  | C | H |
| calculated (%) | 74.58 | 10.52 |
| observed (%) | 74.74 | 10.66 |

Mass (m/z): 402(M+).

$^1$H-NMR(CDCl$_3$): δ0.84(3H, d, J=7), 0.87(6H, d, J=7), 0.9-1.9(14H), 1.29(3H, d, J=8), 2.1-2.8(4H, m), 3.0-3.6(5H, m), 4.22(2H, d, J=4), 7.0-7.5(5H).

EXAMPLE 24

4-Isobutylphenylacetic acid

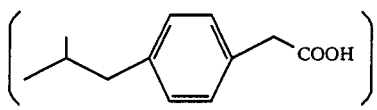

17.8 g of 4-isobutylbenzoic acid was reduced by the use of lithium aluminum hydride and concentrated. The concentration residue was dissolved in 30 ml of pyridine, followed by the addition of 22.0 g of p-toluenesulfonyl chloride under cooling with ice. The reaction mixture was poured into ice-water and extracted with ether. The extract was washed with water and concentrated at 30° C.

10.0 g of potassium cyanide was suspended in 150 ml of DMSO. The above concentration residue was added to the obtained suspension at 120° C. to carry out the reaction for several hours. The reaction mixture was cooled, poured into ice-water and extracted with ether. The extract was washed with water and concentrated.

The residue was dissolved in 100 ml of propylene glycol, followed by the addition of 17 g of potassium hydroxide. The resulting mixture was stirred at 120° C. for several hours, cooled, poured into ice-water, neutralized with dilute hydrochloric acid and extracted with ether. The extract was washed with water, concentrated and recrystallized from hexane to obtain 5.4 g of the objective compound as a white crystal (yield: 28%).

| Elemental analysis as $C_{12}H_{16}O_2$ | | |
|---|---|---|
| | C | H |
| calculated (%) | 74.97 | 8.39 |
| observed (%) | 75.11 | 8.57 |

Mass(m/z): 192(M+).

$^1$H-NMR(CDCl$_3$): δ0.90(6H, d, J=8), 1.7–2.1(1H), 2.52(2H, d, J=8), 3.53(2H, s), 7.0–7.2(4H).

EXAMPLE 25

4-(2′,6′-Dimethylheptyl)phenylacetic acid

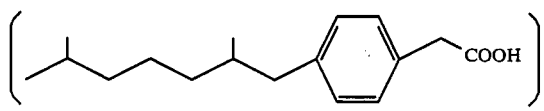

24.8 g of 4-(2′,6′-dimethylheptyl)benzoic acid was used as a starting material and treated according to the same procedure as the one described in Example 24 to obtain 5.8 g of the objective compound as a white crystal (yield: 22%).

| Elemental analysis as $C_{17}H_{26}O_2$ | | |
|---|---|---|
| | C | H |
| calculated (%) | 77.82 | 9.99 |
| observed (%) | 78.01 | 10.05 |

Mass(m/z): 262(M+).

$^1$H-NMR(CDCl$_3$): δ0.85(3H, d, J=7), 0.87(6H, d, J=7), 1.0–1.9(8H), 2.2–2.9(2H, m), 3.51(2H, s), 7.0–7.2(4H).

EXAMPLE 26

4-(2′,6′,10′-Trimethylundecyl)phenylacetic acid

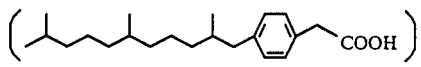

31.8 g of 4-(2′,6′,10′-trimethylundecyl)benzoic acid was used as a starting material, treated according to the same procedure as the one described in Example 24 and purified by chromatography to obtain 11.6 g of the objective compound as a wax (yield: 35%).

| Elemental analysis as $C_{22}H_{36}O_2$ | | |
|---|---|---|
| | C | H |
| calculated (%) | 79.46 | 10.91 |
| observed (%) | 79.66 | 11.08 |

Mass(m/z): 332(M+).

$^1$H-NMR(CDCl$_3$): δ0.81(3H, d, J=7), 0.85(9H, d, J=7), 1.0–1.9(15H), 2.2–2.9(2H, m), 3.53(2H, s), 7.0–7.2(4H).

What is claimed is:

1. A pharmaceutical composition having antihypercholesterolemic activity or antiarteriosclerotic activity, which comprises a polyprenyl compound having the formula:

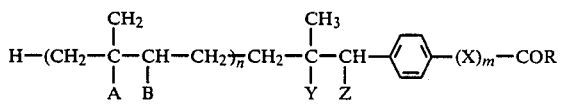

wherein A, B, Y and Z are hydrogens, or the pair A and B, and the pair Y and Z, each form a single valence bond between the carbon atoms to which they are attached, n is an integer of 0 to 2, X is a group having the formula

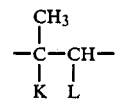

wherein K and L are hydrogens or the pair K and L forms a single valence bond between the carbon atoms to which they are attached, a group having the formula —CH$_2$— or a group having the formula —(CH$_2$)$_2$—, m is an integer of 0 or 1, and R is hydroxy, a group having the formula

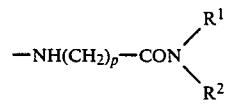

wherein R$^1$ and R$^2$ are the same or different and each is hydrogen or lower alkyl and p is an integer of 1 or 2, a group having the formula —NH—(CH$_2$)$_q$—OH wherein q is an integer of 1 or 2, or a group having the formula

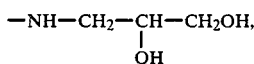

or a pharmacologically acceptable salt thereof, and a pharmaceutically acceptable carrier.

2. A composition as defined in claim 1, wherein R is OH.

3. A composition as defined in claim 1, wherein X is

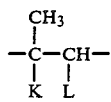

and R is OH.

4. A composition as defined in claim 1, wherein X is

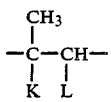

and R is

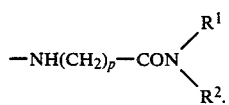

5. A composition as defined in claim 1, wherein X is

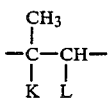

and R is —NH—(CH$_2$)$_q$—OH.

6. A composition as defined in claim 1, wherein X is

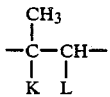

and R is

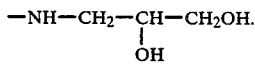

7. A composition as claimed in claim 1 in which said compound is selected from the group consisting of:
4-(1'-Isobutenyl)benzoic acid,
4-Isobutylbenzoic acid,
4-(2',6'-Dimethyl-1',5'-heptadienyl)benzoic acid,
4-(2',6'-Dimethylheptyl)benzoic acid,
4-(2',6',10'-Trimethylundecyl)benzoic acid,
3-(4'-(1''-Isobutenyl)phenyl)-2-butenoic acid,
3-(4'-Isobutylphenyl)-2-butenoic acid,
3-(4'-Isobutylphenyl)butyric acid,
3-(4'-(2'',6''-Dimethyl-1'',5''-heptadienyl)-phenyl)-2-butenoic acid,
3-(4'-(2'',6''-Dimethylheptyl)phenyl)-2-butenoic acid,
3-(4'-(2'',6''-Dimethylheptyl)phenyl)acetic acid
3-(4'-(2'',6'',10''-Trimethylundecyl)phenyl)-2-butenoic acid,
3'(4'-(2'',6'',10''-Trimethylundecyl)phenyl)-butyric acid,
3-(4'-Isobutylphenyl)propionic acid,
3-(4'-(2'',6''-Dimethylheptyl)phenyl)propionic acid,
3-(4'-(2'',6'',10''-Trimethylundecyl)phenyl)-propionic acid,
3'(4'-(2'',6''-Dimethylheptyl)benzoyl)amino-1,2-propanediol,
N-(4-(2',6'-Dimethylheptyl)benzoyl)glycinamide,
N-(4-(2',6'-Dimethylheptyl)benzoyl)-N',N'-diethylglycinamide,
N-(3-(4'-(2'',6''-Dimethylheptyl)phenyl)butanoyl)-ethanolamine,
3-(3'-(4''-(2''',6'''-Dimethylheptyl)phenyl)-butanoyl)amino-1,2-propanediol,
N-(3'(4'-(2'',6''-Dimethylheptyl)phenyl)butanoyl)-glycinamide,
N-(3-(4'(2'',6''-Dimethylheptyl)phenyl)-butanoyl)N',N'-diethylglycinamide,
4-Isobutylphenylacetic acid,
4-(2',6'-Dimethylheptyl)phenylacetic acid and 4-(2',6',10'-Trimethylundecyl)phenylacetic acid.

8. A composition as defined in claim 1 wherein A, B, Y and Z are hydrogen atoms, n=1, K and L are hydrogen atoms, m=1, R is —NH—(CH$_2$)$_q$—OH and q=1.

9. A composition as defined in claim 1 wherein A, B, Y and Z are hydrogen atoms, n=1, K and L are hydrogen atoms, m=1 and R is a hydroxy group.

10. A method of treating a patient afflicted with hyper cholesterolemia or arteriosclerosis which comprises administering to said patient a therapeutically effective amount of a composition as claimed in claim 1.

11. A process for producing a compound of the formula (I):

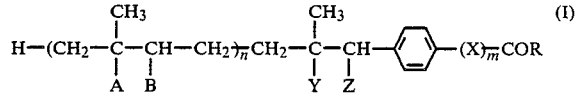

in which
n is zero, 1 or 2; m is zero; R is OH;
A and B form a single bond between both carbon atoms and Y and Z form a single bond between both carbon atoms;
which comprises reacting a compound of the formula (II):

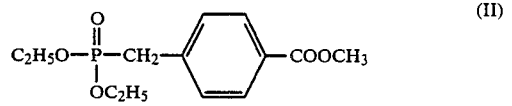

with a compound of the formula (III):

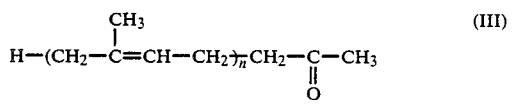

wherein n is zero, 1 or 2.

* * * * *

UNITED STATES PATENT AND TRADEMARK OFFICE
CERTIFICATE OF CORRECTION

PATENT NO. : 4 788 330
DATED : November 29, 1988
INVENTOR(S) : Kouji NAKAMOTO et al It is certified that error appears in the above-identified patent and that said Letters Patent is hereby corrected as shown below:

On the title page, at item [21] change "37,472" to ---837,472---.

Signed and Sealed this

Twentieth Day of June, 1989

Attest:

DONALD J. QUIGG

Attesting Officer

Commissioner of Patents and Trademarks